United States Patent
Ponnusamy

(10) Patent No.: US 8,399,600 B2
(45) Date of Patent: Mar. 19, 2013

(54) PREPARATION OF LOW MOLECULAR WEIGHT POLYLYSINE AND POLYORNITHINE IN HIGH YIELD

(75) Inventor: Ettigounder Ponnusamy, Ballwin, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 319 days.

(21) Appl. No.: 12/863,131

(22) PCT Filed: Jul. 29, 2009

(86) PCT No.: PCT/US2009/052085
§ 371 (c)(1),
(2), (4) Date: Jul. 15, 2010

(87) PCT Pub. No.: WO2010/017075
PCT Pub. Date: Feb. 11, 2010

(65) Prior Publication Data
US 2011/0054146 A1    Mar. 3, 2011

Related U.S. Application Data

(60) Provisional application No. 61/087,031, filed on Aug. 7, 2008.

(51) Int. Cl.
*C08G 69/10* (2006.01)
(52) U.S. Cl. .................................................. 528/328
(58) Field of Classification Search .................. 528/328;
424/43, 45, 46; 530/324
See application file for complete search history.

(56) References Cited

U.S. PATENT DOCUMENTS

| | | |
|---|---|---|
| 3,350,365 A | 10/1967 | Wakasa et al. |
| 3,594,351 A | 7/1971 | Uchida et al. |
| 3,635,909 A | 1/1972 | Fujimoto et al. |
| 4,450,150 A | 5/1984 | Sidman |
| 4,686,295 A | 8/1987 | Youssefyeh et al. |
| 5,258,446 A | 11/1993 | Enomoto et al. |
| 5,571,940 A | 11/1996 | Palacios |
| 5,654,381 A | 8/1997 | Hrkach et al. |
| 5,767,227 A | 6/1998 | Latham et al. |
| 6,048,565 A | 4/2000 | Getler et al. |
| 6,048,898 A | 4/2000 | Konfino et al. |
| 6,362,161 B1 | 3/2002 | Konfino et al. |
| 6,410,057 B1 | 6/2002 | Kweon-Choi et al. |
| 6,479,665 B2 | 11/2002 | Cornille et al. |
| 6,515,017 B1 | 2/2003 | Li et al. |
| 6,603,016 B2 | 8/2003 | Cornille et al. |
| 6,620,847 B2 | 9/2003 | Konfino et al. |
| 6,630,171 B1 | 10/2003 | Huille et al. |
| 6,656,458 B1 | 12/2003 | Philippe et al. |
| 6,670,447 B2 | 12/2003 | Tsunoda et al. |
| 6,680,365 B1 | 1/2004 | Deming |
| 6,686,446 B2 | 2/2004 | Deming et al. |
| 6,939,539 B2 | 9/2005 | Konfino et al. |
| 7,049,399 B2 | 5/2006 | Bejan et al. |
| 7,074,580 B2 | 7/2006 | Gad et al. |
| 7,163,802 B2 | 1/2007 | Gad et al. |
| 7,199,098 B2 | 4/2007 | Konfino et al. |
| 7,294,719 B2 | 11/2007 | Carubia et al. |
| 7,317,070 B1 | 1/2008 | Ponnusamy |
| 7,495,072 B2 | 2/2009 | Dolitzky |
| 7,560,100 B2 | 7/2009 | Pinchasi et al. |
| 7,625,861 B2 | 12/2009 | Konfino et al. |
| 2003/0147958 A1 | 8/2003 | Ahn et al. |
| 2006/0052586 A1 | 3/2006 | Dolitzky |
| 2006/0069230 A1 | 3/2006 | Papisov |
| 2006/0106229 A1 | 5/2006 | Carubia et al. |
| 2006/0122113 A1 | 6/2006 | Pinchasi et al. |
| 2006/0154862 A1 | 7/2006 | Ray et al. |
| 2007/0054857 A1 | 3/2007 | Pinchasi et al. |
| 2007/0141663 A1 | 6/2007 | Ding et al. |
| 2008/0015332 A1 | 1/2008 | Bryson et al. |
| 2008/0021192 A1* | 1/2008 | Iyer et al. ...................... 528/314 |
| 2008/0021200 A1 | 1/2008 | Ray et al. |
| 2008/0125581 A1 | 5/2008 | Deming et al. |
| 2010/0034566 A1 | 2/2010 | Kim et al. |
| 2010/0036092 A1 | 2/2010 | Hsiao et al. |
| 2010/0160606 A1 | 6/2010 | Luten |
| 2010/0174048 A1 | 7/2010 | Ray et al. |
| 2010/0234272 A1 | 9/2010 | Ray et al. |
| 2010/0256039 A1 | 10/2010 | Coleman et al. |
| 2012/0071612 A1 | 3/2012 | Ponnusamy |
| 2012/0123094 A1 | 5/2012 | Ponnusamy |

FOREIGN PATENT DOCUMENTS

| | | |
|---|---|---|
| WO | 9200748 A1 | 1/1992 |
| WO | 2006029411 A2 | 3/2006 |
| WO | 2006050122 A1 | 5/2006 |
| WO | 2007022193 A2 | 2/2007 |
| WO | 2007059342 A2 | 5/2007 |
| WO | 2008006026 A1 | 1/2008 |
| WO | 2009017775 A2 | 2/2009 |
| WO | 2009129018 A1 | 10/2009 |
| WO | 2010017075 A1 | 2/2010 |
| WO | 2010017929 A1 | 2/2010 |
| WO | 2010072418 A1 | 7/2010 |
| WO | 2010104789 A1 | 9/2010 |
| WO | 2010115175 A1 | 10/2010 |
| WO | 2012/067974 A1 | 5/2012 |

OTHER PUBLICATIONS

Deming, "Polypeptide and Polypeptide Hybrid Copolymer Synthesis via NCA Polymerization", Advances in Polymer Science, 2006, pp. 1-18, vol. 202.

(Continued)

*Primary Examiner* — Gregory Listvoyb

(57) ABSTRACT

The present invention generally relates to the large-scale (e.g., greater than 1 kg scale) preparation of low molecular weight polylysine or polyornithine in high yield by preparing a polylysine or polyornithine having a weight average molecular weight from about 12,500 Daltons to about 22,000 Daltons and hydrolyzing it to produce a polylysine or polyornithine having a weight average molecular weight from about 5,500 Daltons to about 12,000 Daltons. In preferred embodiments, the polymer is a homopolymer of poly-L-lysine.

19 Claims, No Drawings

OTHER PUBLICATIONS

International Search Report and Written Opinion for PCT/US10/26520, dated May 3, 2010, 8 pgs.

International Search Report and Written Opinion mailed Mar. 26, 2012 for related International Patent Application No. PCT/US2011/060507, 9 pgs.

Goodman et al., "a-Amino Acid n-Carboxyanhydride Polymerizations—A Mechanistic Analysis", Pure and Applied Chemistry, 1981, pp. 699-714, vol. 53.

Rodriguez-Hernandez et al., "Highly Branched Poly(L-lysine)", Biomacromolecules, 2003, pp. 249-258, vol. 4.

Van Dijk-Wolthuis et al., "Synthesis and characterization of poly-L-lysine with controlled low molecular weight", Macromolecular Chemistry and Physics, 1997, pp. 3893-3906, vol. 198, No. 12.

International Search Report for PCT/US09/52085 dated Sep. 15, 2009, 1 page.

Waley, S.G., et al., "The action of trypsin on polylysine," The Biochemical Journal, Sep. 1953, pp. 328-337, vol. 55, No. 2.

Extended European Search Report issued Feb. 2, 2012 in European Patent Application No. 09805374.7, 8 pages.

* cited by examiner

PREPARATION OF LOW MOLECULAR WEIGHT POLYLYSINE AND POLYORNITHINE IN HIGH YIELD

CROSS REFERENCE TO RELATED APPLICATIONS

This application is the United States national stage of International Application No. PCT/US2009/052085, filed Jul. 29, 2009, which claims the benefit of U.S. Provisional Application No. 61/087,031, filed Aug. 7, 2008, the entire content of each of which is hereby incorporated herein by reference.

FIELD OF THE INVENTION

The present invention generally relates to the preparation of large-scale (greater than 1 kg scale) low molecular weight polylysine or polyornithine in high yield by preparing a polylysine or polyornithine intermediate having a lysine- or ornithine-basis weight average molecular weight from about 12,500 Daltons to about 22,000 Daltons and hydrolyzing it to produce a polylysine or polyornithine having a weight average molecular weight from about 5,500 Daltons to about 12,000 Daltons. In preferred embodiments, the process is used to prepare polylysine. In some of these embodiments, the polymer is a homopolymer of poly-L-lysine.

BACKGROUND OF THE INVENTION

Polylysine and polyornithine are known and are under investigation as DNA condensing agents to be used in non-viral gene therapy. However, as is known in the literature, poly-L-lysine has cytotoxic effects that decrease with decreasing molecular weight. Thus, preparation of a low molecular weight polylysine is desirable.

Poly-L-lysine and other polyamino acids have been prepared by a variety of routes. Commercially, poly-L-lysine has been prepared by reaction of $N^\epsilon$-carbobenzyloxy(Cbz)-L-Lysine, N-carboxyanhydride with a polymerization initiator to produce poly-$N^\epsilon$-Cbz-L-lysine. The poly-$N^\epsilon$-Cbz-L-lysine is treated with hydrobromic acid in acetic acid to remove the Cbz group and form poly-L-lysine having a molecular weight of about 7,000 Daltons. The product can be dialyzed, lyophilized, and recovered in an 11-30% yield. This yield of the current process is variable and is unacceptably low. Thus, a need exists for higher yield large-scale processes having less variability to produce polylysine having a lysine-basis weight average molecular weight from about 5,500 Daltons to about 12,000 Daltons.

SUMMARY OF THE INVENTION

Among the various aspects of the invention is a process for preparing a large-scale relatively low molecular weight polylysine or polyornithine in high yield.

Another aspect of the invention is a process for the preparation of a polylysine or polyornithine polymer comprising repeating units corresponding to Formula 3 or a salt thereof and having a lysine- or ornithine-basis weight average molecular weight from about 5,500 to about 12,000 Daltons. The process comprises hydrolyzing a polylysine or polyornithine intermediate comprising repeating units corresponding to Formula 3 or a salt thereof and having a lysine- or ornithine-basis weight average molecular weight from about 12,500 to about 22,000, wherein Formula 3 has the structure:

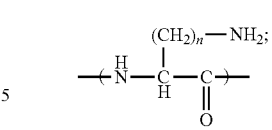

Formula 3 and n is 3 or 4.

The process of the invention described above further comprises removing the nitrogen protecting group from a protected polylysine or polyornithine intermediate comprising repeating units of Formula 2 or a salt thereof and having a lysine- or ornithine-basis weight-average molecular weight of from about 12,500 Daltons to about 22,000 Daltons, wherein Formula 2 has the structure

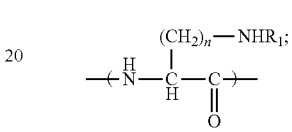

Formula 2

$R_1$ is an amino protecting group; and n is 3 or 4.

The various processes described above can further comprise preparation of the protected polylysine or polyornithine intermediate by polymerizing an N-carboxyanhydride compound of Formula 1, wherein Formula 1 has the structure

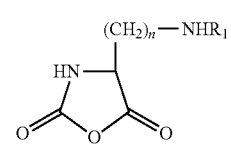

Formula 1

$R_1$ is an amino protecting group; and n is 3 or 4.

Other objects and features will be in part apparent and in part pointed out hereinafter.

DESCRIPTION OF THE PREFERRED EMBODIMENTS

Advantageously, polylysine or polyornithine can be prepared in accordance with the process of the present invention in a relatively more efficient and/or productive manner. In general, the polylysine or polyornithine polymer comprises repeating units corresponding to Formula 3, $N^\epsilon$-salts, or $N^{\delta}$-salts thereof:

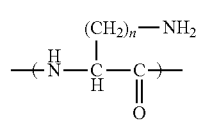

Formula 3 wherein n is 3 (i.e., polyornithine) or 4 (i.e., polylysine). The polylysine or polyornithine polymer product comprises a mixture of molecules having repeating units of Formula 3 to form a polymer having a lysine- or ornithine-basis weight average molecular weight of from about 5,500 Daltons to about 12,000 Daltons.

Generally, the homopolymers of polylysine can be comprised of D-, L-, or a racemic mixture of isomers of the lysine repeat units. In preferred embodiments, the polylysine comprises poly-L-lysine. Further, the homopolymers of polyornithine can be comprised of D-, L-, or a racemic mixture of isomers of the ornithine repeat units. In preferred embodiments, the polyornithine comprises poly-L-ornithine. The stereochemistry of the polylysine or polyornithine is determined by the stereochemistry of the starting monomer. The structures of Formulae 1, 2, and 3 represent monomers and polymers having a D-, L-, or a mixture of D- and L-stereochemistry.

Regardless of the composition of the repeat units, the process of the present invention enables the preparation of polylysine having a weight average lysine-basis molecular weight of from about 5,500 Daltons to about 12,000 Daltons. For certain applications, polylysine having an average lysine-basis molecular weight of about 7,000 Daltons to about 10,000 Daltons are desired. The process also enables the preparation of polyornithine having a weight average ornithine-basis molecular weight of from about 5,500 Daltons to about 12,000 Daltons.

For purposes of this application, the weight average molecular weight is determined using the gel permeation chromatography with multi-angle laser light scattering (GPC MALLS) technique that provides an absolute weight average molecular weight and polydispersity index.

Polymerization

The polylysine or polyornithine of the present invention may be prepared by a process that begins with polymerization of a N-carboxyanhydride of an $N^\epsilon$-protected lysine or an $N^{\delta}$-protected ornithine, in a polymerization medium comprising a suitable solvent. Polymerization is preferably conducted in the presence of a polymerization initiator contained in the reaction medium.

The preparation of N-carboxyanhydrides of protected lysines and ornithines is known. In general, the protected lysine or ornithine is treated with phosgene in an ethereal solvent (e.g., tetrahydrofuran) to produce the corresponding $N^\epsilon$-protected-lysine, N-carboxyanhydride or $N^{\delta}$-protected-ornithine, N-carboxyanhydride. In certain embodiments, the $N^\epsilon$-protected-lysine, N-carboxyanhydride or $N^{\delta}$-protected-ornithine, N-carboxyanhydride corresponds to Formula 1

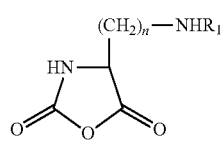

Formula 1 wherein $R_1$ is amino protecting group and n is 3 or 4. $R_1$, for example, can be carbobenzyloxy (Cbz), t-butyloxycarbonyl (t-Boc), or allyloxycarbonyl. Preferably, $R_1$ is carbobenzyloxy (Cbz). Thus, for example, in one embodiment, the N-carboxyanhydride is the N-carboxyanhydride of Cbz-lysine or Cbz-ornithine and corresponds to Formula 1A.

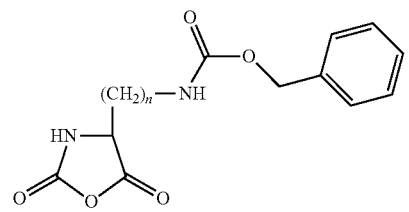

Formula 1A

In general, the polymerization initiator is a nucleophile. In addition, the polymerization initiator preferably possesses physical properties, which enable the initiator to be separated from the product polymer or otherwise eliminated from the reaction mixture upon the completion of the polymerization reaction. Exemplary polymerization initiators include metal alkoxides having the formula MOR, wherein M is a metal and R is an alkyl group. For example, the metal may be sodium or potassium. By way of further example, the alkyl moiety may be a linear, branched or cyclic group having 1 to 10 carbon atoms. Presently preferred polymerization initiators include sodium methoxide, sodium ethoxide, sodium propoxide, potassium methoxide, potassium ethoxide, potassium propoxide, or combinations thereof. Sodium methoxide is presently particularly preferred.

The molar ratio of the N-carboxyanhydride ("NCA") to the polymerization initiator used to form the polymerization reaction mixture may vary over a relatively wide range. It is generally preferred that the molar ratio of the NCA to the initiator be in the range of about 5:1 to about 15:1; preferably, about 8:1 to about 12:1, respectively.

The solvent used in the polymerization reaction mixture may generally be any suitable solvent. Exemplary solvents include dioxane, chloroform, dichloromethane, acetonitrile, and combinations thereof. Preferably, the initial N-carboxyanhydride monomer is mixed with the solvent to provide a monomer concentration between about 0.2 M and about 1 M; preferably about 0.4 M to about 0.6 M; or between about 0.02 wt. % to about 0.13 wt. %; preferably, between about 0.05 wt. % to about 0.1 wt. %.

The reaction temperature of the polymerization of the N-carboxyanhydride is not narrowly critical. The reaction may be carried out over a range of temperatures and times depending on the solvent used. The reaction conditions (e.g., solvent, pressure, and temperature) are selected in order to provide a reaction rate that is not too slow and to minimize loss of solvent due to evaporation. For example, polymerization may be carried out for a period of about 12 to about 30 hours, more typically about 18 hours to 24 hours, at a temperature of about 20° C. to about 40° C., more typically about 25° C. to about 30° C., and preferably at about 25° C.

The resulting polymer contains protected lysine or ornithine repeating units. For example, these repeat units may generally correspond to Formula 2

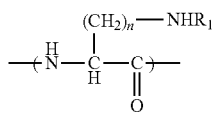

Formula 2 wherein $R_1$ and n are as defined above in connection with Formula 1. In various preferred embodiments, when the repeating unit is a protected lysine, the amino protecting group is Cbz, the protected polylysine repeating unit generally corresponds to Formula 2A.

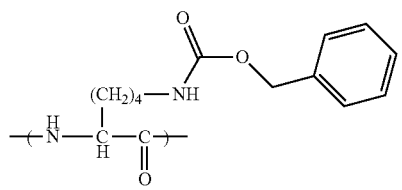

Formula 2A

Upon completion of polymerization, the polyamino acid can be precipitated in water and filtered, but typically the polymerized protected polymer is diluted with solvent to a concentration of about 0.05 M to about 0.5 M (or about 0.0064 wt. % to about 0.064 wt. %) protected polylysine intermediate (based on the amount of the NCA starting material); preferably, from about 0.1 M to about 0.3 M. The product of the polymerization is a protected polylysine or polyornithine intermediate, preferably a protected lysine homopolymer, typically having a lysine-basis weight average molecular weight between about 12,500 and about 22,000 Daltons.

Removing the Amino Protecting Group

The amino protecting group can be removed by catalytic hydrogenation or treatment with a strong acid. These strong acids can include hydrobromic acid, hydrochloric acid, hydroiodic acid, sulfuric acid, and the like. In various preferred embodiments, the amino protecting group is removed by treatment with anhydrous hydrobromic acid. When the amino protecting group is removed, the polylysine or polyornithine contains repeat units of Formula 3

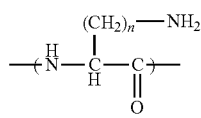

Formula 3 wherein n is as defined above in connection with Formula 1. In general, the number of repeating units varies depending the specific process conditions. Under the conditions prevailing in the deprotection reaction, the number of repeating units provides a lysine-basis or ornithine-basis weight average molecular weight from about 12,500 Daltons to about 22,000 Daltons.

In the removal of the amino protecting group, the $N^\epsilon$-substituted polylysine or $N^{67}$-substituted polyornithine intermediate is preferably contacted with a strong acid. Where the polymerization reaction has been conducted in a solvent medium, this solution may be diluted to provide a reaction medium for the deprotection step. The polymerization reaction product is preferably diluted with the same solvent that has been used for the polymerization, to produce a solution having a concentration of about 0.05 M to about 0.5 M; preferably from about 0.1 M to about 0.3 M (or about 0.0064 wt. % to about 0.064 wt. %) protected polylysine intermediate (based on the amount of the NCA starting material) for use in the deprotection step. Alternatively, the protected polylysine or polyornithine intermediate may have been precipitated from the polymerization reaction solution and redissolved in the desired solvent to produce a solution in the latter concentration range preparatory to the deprotection step.

To carry out the deprotection reaction, the strong acid in a solvent or alone, may be introduced into the deprotection reaction medium. Preferably, the strong acid is introduced into the deprotection reaction medium in a weight ratio to the $N\epsilon$-protected polylysine or $N^{67}$-protected polyornithine (based on the NCA starting material) between about 2:1 and about 4:1. In some cases, a solution of a strong acid comprising between about 20 wt. % and about 40 wt. % strong acid (e.g., HBr) and between about 60 wt. % and about 80 wt. % solvent (e.g., acetic acid) and introduced into the polymerization medium. Preferably, a 30 to 35 wt. % hydrobromic acid in acetic acid solution is used as the source of HBr; this mixture typically contains between 0.5 and 1.5 wt. % water. Typically, the strong acid is preferably added relatively slowly, e.g., over a period of about 45 to about 90 minutes (essentially dropwise on a laboratory scale), and the polymerization reaction mixture is agitated to assure uniform mixing.

The reaction temperature of the deprotection step is not narrowly critical. Preferably, the reaction is conducted at a temperature about 20° C. to about 40° C.; more preferably, at about 25° C. to about 30° C.; typically at about 25° C. Typically, the deprotection step requires approximately 15 to 20 hours, most typically 18 hours of reaction.

The deprotection step produces the polylysine or polyornithine intermediate in the form of an $N^\epsilon$- or $N^{67}$-mineral acid salt, which precipitates from the mixed organic deprotection reaction medium. This salt is separated from the supernatant liquid, as by filtration, and the solids washed with an organic solvent, preferably a polar solvent such as acetone, to remove the major side product of benzyl bromide. The deprotected polylysine or polyornithine intermediate salt or its free base may then be taken up in an aqueous medium and hydrolyzed to yield the polylysine or polyornithine polymer product. Where a strong acid is used for the hydrolysis, the polylysine polymer product is also produced in the form of its $N^\epsilon$ or $N^\delta$ mineral acid salt.

Even after the solvent wash, the deprotection reaction product typically remains contaminated with oligomers, lower molecular weight salts and other low molecular weight by-products. Prior to the hydrolysis reaction, the deprotection reaction product may be further purified by taking it up into an aqueous medium and subjecting it to dialysis or ultrafiltration. A dialysis feed mixture comprising an aqueous solution of the deprotection reaction product, e.g., in a concentration between about 0.5 and about 1.5 wt. %, is placed in contact with a surface of dialysis membrane, or an ultrafiltration membrane that has a carrier liquid, e.g., a flowing deionized water stream, in contact with its opposite face. For ultrafiltration, a pressure differential of between about 20 psi (138 kPa) and about 30 psi (207 kPa) may be established across the membrane to promote flow of a permeate comprising low molecular weight components and solvent through the membrane to the carrier solution. Transport of oligomers and low molecular weight contaminants to the carrier liquid leaves a retentate comprising deprotected polylysine intermediate of reduced oligomer content.

The retentate may be diluted with water, preferably deionized, to provide a solution typically comprising 0.03 wt. % to a 0.1 wt. % deprotected polylysine that may be used as the feed material to the hydrolysis step. Alternatively, the retentate may be lyophilized to yield a dry solid deprotected polylysine, which may then be redissolved in an aqueous medium to provide conveniently a solution of the aforesaid concentration that is sent to the hydrolysis step.

Hydrolysis to Reduce the Polymer Molecular Weight

Hydrolysis is conducted by contacting the deprotected polylysine intermediate in an aqueous hydrolysis reaction medium with a strong acid (e.g., hydrochloric acid, hydrobromic acid; hydroiodic acid, sulfuric acid, and the like) preferably having a concentration between about 0.1 M and about 0.5 M in the aqueous medium. The ratio of strong acid to deprotected polylysine intermediate for the hydrolysis is preferably between about 1:5 and about 1:1. To establish the desired strong acid concentration in the reaction medium, a strong acid source such as HBr may conveniently be introduced into the hydrolysis reaction medium in a source solution having a concentration in the range of 40 wt. % to 68 wt. %. Hydrolysis is preferably conducted at a temperature between about 25° C. and about 30° C. and produces a polylysine or polyornithine polymer having a lysine- or ornithine-basis weight average molecular weight from about 5,500 Daltons to about 12,000 Daltons from polylysine or polyornithine having a lysine- or ornithine-basis weight average molecular weight from about 12,500 Daltons to about 22,000 Daltons. Because the hydrolysis reaction proceeds progressively as long as the polylysine or polyornithine remains in contact with the strong acid under the aforesaid conditions, there is a need to establish the end point of the reaction so that the lysine- or ornithine-basis weight average molecular weight of the polylysine or polyornithine polymer product falls within the target range, preferably 5,500 to 12,000 Daltons. In accordance with the process of the invention, the end point of the hydrolysis reaction may be estimated based on the viscosity of a sample solution of dialyzed and lyophilized deprotected polylysine or polyornithine intermediate. If the entire quantity of deprotected polylysine or polyornithine intermediate has been purged of oligomers and low molecular weight contaminants by dialysis and the retentate then lyophilized, a sample of this lyophilized intermediate can be used for the end point projection. Otherwise, a sample of the unpurified deprotected polylysine or polyornithine intermediate may be taken and subjected to dialysis and lyophilization on a laboratory scale to provide the specimen used in end point projection.

To estimate the desired hydrolysis reaction time, a test solution is prepared consisting of a 1% by lysine- or ornithine-basis weight aqueous solution of the dialyzed and lyophilized sample or specimen of dialyzed and lyophilized deprotected polylysine or polyornithine intermediate, and the viscosity of this solution is determined at 25° C. The viscosity of the sample is determined by adding 10 mL of the solvent to a Cannon-Fenske, size 50 viscometer, placing the viscometer in a constant temperature water bath having a temperature of 25±0.1° C. and vertically aligning the capillary tube of the viscometer with a weighted thread on the outside of the bath. The viscometer temperature is allowed to reach equilibrium over 20 minutes, the solvent is drawn into the tube to just above mark M (see FIG. 1). The time in seconds for the meniscus to pass from mark M to mark N is the efflux time, $t_0$, for the solvent. At least four successive readings are made of the flow time until the average deviation from the mean is less than ±0.1 second. The viscometer is cleaned and the process above is repeated using the 1 wt. % aqueous solution of the polymer product to get the efflux time, t, for the sample. The relative and specific viscosities are calculated using the following equations.

Relative viscosity$(\eta_r)=t/t_0$

Specific viscosity$(\eta_{sp})=\eta_r-1$

To calculate the viscosity molecular weight, the equation below is used (see A. Aaron and A. Berger, Biochim. Biophys. Acta, volume 69, page 397 (1963)). This equation was developed for polylysine, but polylysine and polyornithine are chemically similar with polyornithine having one fewer methylene group in its repeat unit, the same equation can be used.

Degree of Polymerization(DP)=log$^{-1}$[log$(\eta_{sp}/c)\times$ 0.79+2.46]

The variable, $\eta_{sp}$, is the specific viscosity and c is the concentration of the polymer solution. The molecular weight is calculated using the following equations.

Molecular weight=DP×209(for Polylysine.HBr)

Molecular weight=DP×195(for Polyornithine.HBr)

The time required to hydrolyze the polymer to the desired weight average molecular weight of 5,500 to 12,000 Daltons (measured by GPC MALLS) may then be calculated using the following formula:

Time required=[(Viscosity Molecular Weight of unhydrolyzed polymer−21,000)×0.012]+72(±10%) Hours.

The 21,000 and 0.012 are factors that have been determined empirically. It will be understood that selection of 1 wt. % as the concentration of the polylysine or polyornithine in the test solution is arbitrary and that any concentration that yields a reasonable viscosity versus molecular weight gradient is acceptable. However, the constants in the reaction time algorithm set forth above apply only to the case of a 1 wt. % solution. For any other concentration the constants of the equation would need to be determined by correlation of empirical data.

Once the time of hydrolysis is determined, the unhydrolyzed polymer is dissolved in deionized water to form a clear solution, mixed for 10 minutes, and the strong acid is added and mixed for the calculated time. Typically, the reaction time for the hydrolysis reaction is from about 100 hours to about 350 hours. The hydrolysis reaction is carried out to the extent required to produce a polymer having a repeat unit of Formula 3 and a weight average molecular weight of from about 5,500 Daltons to about 12,000 Daltons. The polydispersity index (PDI) is calculated by dividing the weight average molecular weight by the number average molecular weight. The PDI indicates the distribution of individual molecular masses in a batch of polymers. The PDI for polylysine made by the process described above is 1.2 to 1.5.

After a polylysine or polyornithine product having the desired lysine- or ornithine-basis weight average molecular weight has been formed, this product may be further purified by dialysis or ultrafiltration. To prepare for dialysis, the hydrolysis reaction solution may be diluted with water in a volumetric ratio between 30 parts hydrolysis reaction solution and 70 parts water to 70 parts hydrolysis reaction solution and 30 parts water. Preferably the ratio is between 40:60 and 60:40, conveniently about 50:50. The dilute solution is then placed in contact with one surface of a dialysis or ultrafiltration membrane while an aqueous carrier solution is placed in contact with the opposite side of the membrane. For ultrafiltration, a pressure differential between about 20 psi (138 kPa) and about 30 psi (207 kPa) may be established across the membrane to promote flow of a permeate comprising low molecular weight components and solvent through the membrane to the carrier solution. The dialyzed product is collected and preferably lyophilized to yield the polylysine or polyornithine having repeat units of Formula 3 in its commercially acceptable form.

The yield of the hydrolyzed polylysine having a lysine-basis weight average molecular weight from about 5,500 to about 12,000 Daltons is typically greater than about 45% based on the amount of the NCA starting material. In certain embodiments, the yield of the hydrolyzed polylysine has been found to range from about 45% to about 55% based on the amount of the NCA starting material. It has been observed that experiments to produce polylysine having a lysine-basis weight average molecular weight from about 5,500 to about 12,000 Daltons in the polymerization step required more polymerization initiator and provided a lower yield. Without being bound by theory, it is hypothesized that the greater concentration of polymerization initiator initiated growth of more polymer chains than with a lower concentration of polymerization initiator and consequently, because the NCA monomer could add to relatively more growing chains, the polymer product had many chains that were of a lysine-basis weight average molecular weight below the desired 5,500 Daltons. The necessary removal of these, as by dialysis or ultrafiltration, resulted in poor yields. By comparison, when the process of the present invention is used to prepare a higher molecular weight polymer that is hydrolyzed to provide the desired weight average molecular weight, a lower concentration of polymerization initiator is used in the polymerization of the NCA and there is a smaller amount of undesirably low molecular weight polymer products formed. Further, it has been observed that longer polymer chains are hydrolyzed first and that control of the hydrolysis reaction time can empirically control the weight average molecular weight of the hydrolyzed polymer product.

In various embodiments, removing the nitrogen protecting group from a protected polylysine or polyornithine intermediate comprising repeating units of Formula 2 and hydrolyzing the polylysine or polyornithine intermediate are carried out concurrently. This can be by using the same reagent to remove the nitrogen protecting group and hydrolyze the polylysine or polyornithine.

Definitions

As used herein, the "amino protecting groups" described herein are moieties that block reaction at the protected amino group while being easily removed under conditions that are sufficiently mild so as not to disturb other substituents of the various compounds. For example, the amino protecting groups may be carbobenzyloxy (Cbz), t-butyloxycarbonyl (t-Boc), allyloxycarbonyl and the like. A variety of protecting groups for the amino group and the synthesis thereof may be found in "Protective Groups in Organic Synthesis" by T. W. Greene and P. G. M. Wuts, John Wiley & Sons, 1999.

The term "lysine-basis molecular weight" refers to the molecular weight of either the polylysine polymer itself, the deprotected polylysine intermediate, or the $N^\epsilon$-protected polylysine intermediate as expressed in terms of the equivalent weight of unprotected polylysine free base. The term "ornithine-basis molecular weight" refers to the molecular weight of either the polyornithine polymer itself, the deprotected polyornithine intermediate, or the $N^{67}$-protected polyornithine intermediate as expressed in terms of the equivalent weight of unprotected polyornithine free base. Expression of molecular weight on this basis is preferred because of the substantial differences in molecular weight between repeating units of Formula 3 vs. Formula 2 as well as differences between Formula 3 as depicted and the mineral acid salts thereof.

Having described the invention in detail, it will be apparent that modifications and variations are possible without departing from the scope of the invention defined in the appended claims.

EXAMPLES

The following non-limiting examples are provided to further illustrate the present invention.

The techniques used for the polymerization of the N-carboxyanhydrides (NCA) to polymers are known to those skilled in the art and are given in detail in the review article by M. Goodman and E. Peggion, Pure and Applied Chemistry, volume 53, p. 699, 1981 and the book by H. R. Kricheldorf "Alpha amino acids-N-Carboxyanhydrides and Related Heterocycles", Springer Verlag (1987) and also the recent publications by Wendelmoed N. E. van Dijk-Wolthuis et al, Macromol. Chem. Phys. Volume 198, p. 3893-3906, 1997.

Example 1

Preparation of Poly-L-Lysine.HBr Polymer

Polymerization. $N^{68}$-Cbz-L-Lysine NCA (35 g, 0.114 mole) was dissolved in 0.228 liter of 1,4-dioxane to make a 0.5 M solution. The NCA solution was transferred to a 1 liter three neck round bottom flask equipped with mechanical mixing and a water bath at a temperature of 25 to 30° C. Sodium methoxide (0.0114 moles, 11.4 mL of 1N solution) was placed in 25 mL of 1,4-dioxane. The sodium methoxide solution was added to the NCA solution in one portion with vigorous mixing. The polymerization solution was mixed for 2 hours and held at 25 to 30° C. for 18 to 24 hours.

Deprotection of Cbz group. The protected polymer, Poly-Cbz-L-Lysine was diluted in 1,4-dioxane solution with 340 mL of 1,4-dioxane to make a solution having a 0.2 M concentration based on the amount of the NCA starting material. To this solution was added 70 ml of a solution of 30% hydrobromic acid (HBr) in acetic acid (2 mL/g NCA starting material). This solution was added drop-wise with vigorous mixing in 20 minutes at a temperature of 25 to 30° C. The polymer began precipitating after 40 mL of HBr in acetic acid was added. The resultant mixture was mixed at 25 to 30° C. for 15 minutes to form a uniform slurry. Another 70 mL of HBr in acetic acid (2 ml/g NCA) was added in one lot at 25 to 30° C. and mixed for 18 hours. The mixing was stopped and the precipitate was allowed to settle for 15 minutes. The supernatant was decanted and 350 mL of acetone was added to the precipitate and mixed for 5 minutes. The supernatant was then decanted. This washing step was repeated with 2×175 mL of acetone. Acetone (200 mL) was added and the mixture was filtered on an 11 cm Buchner funnel, washed with 2×100 mL acetone and dried under a nitrogen atmosphere for 5 minutes. The resultant polymer was dissolved in 350 mL deionized water and nitrogen was bubbled through the solution to remove traces of benzyl bromide.

Dialysis/ultrafiltration and lyophilization (freeze drying). The poly-L-lysine.HBr solution was dialyzed or ultrafiltered against running deionized water using dialysis tubing having a molecular weight cut off of approximately 12K or a 5K membrane for ultrafiltration (UF) to remove oligomers and salts. The dialyzed or UF solution was collected, filtered through a 0.2 micron filter, and lyophilized (freeze dried) to get the solid poly-L-lysine.HBr polymer. The yield was 73%. The $^1$H NMR showed the complete removal of the Cbz group (absence of aromatic peak). The viscosity was measured in a 1 wt. % aqueous solution at 25° C. and the viscosity molecular weight was calculated as 26,750 Daltons.

Hydrolysis. The time required to hydrolyze the polymer using 48% aqueous HBr to the desired molecular weight (5,500-12,000 by GPC MALLS) was calculated using the formula:

Time required = [(Viscosity Molecular Weight − 21,000) × 0.012] +

72(±10%) Hours

Number of hours = [(Polymer viscosityMol. Wt. − 21,000) × 0.012] +

72 hours =

(26,750 − 21,000) × 0.012 + 72 hours = 141 hours = 5.875 days

The polymer (16 g) was dissolved in 253 mL deionized water to form a clear solution, the solution was mixed for 10 minutes and 130 mL of 48% HBr (aqueous) was added and mixed for 141 hours.

The hydrolyzed poly-L-lysine.HBr solution was dialyzed or UF against running deionized water using a dialysis tubing having a molecular weight cut off of approximately 12K or a 1K membrane for UF to remove oligomers and salts. The dialyzed or UF solution was collected, filtered through a 0.2 micron filter and lyophilized (freeze dried) to get the solid poly-L-lysine.HBr polymer. The yield was 45.2%. The GPC MALLS measured molecular weight was 7,500 and the viscosity was measured in 1 wt. % aqueous solution at 25° C. to calculate the viscosity molecular weight of 14,400 Daltons.

Example 2

Preparation of Poly-L-Lysine.HBr Polymer

Polymerization. $N^{68}$-Cbz-L-Lys NCA (350.0 g, 1.144 mole) was dissolved in 2.29 liter of 1,4-dioxane to make a 0.5 M solution. The NCA solution was transferred to a 12 liter three-neck round bottom flask equipped with mechanical mixing and a water bath at a temperature of 25 to 30° C. Sodium methoxide (114.4 ml of a 1 N solution, 0.1144 moles) was placed in 100 mL of 1,4-dioxane. The sodium methoxide solution was added to the NCA solution in one portion with vigorous mixing. The polymerization solution was mixed for 2 hours and held at 25 to 30° C. for 18 to 24 hours.

Deprotection of Cbz group. The protected polymer, poly-Cbz-L-Lysine was diluted in 1,4-dioxane solution with 3,430 mL of 1,4-dioxane to make a solution having a 0.2 M concentration based on the amount of NCA starting material. A solution of 30% HBr in acetic acid (700 mL, 2 mL/g NCA starting material) was added to the mixture drop-wise with vigorous mixing over 30 minutes at 25 to 30° C. The polymer started precipitating after about 350 mL of the HBr in acetic acid solution was added. The resultant mixture was mixed at 25 to 30° C. for 15 minutes to form a uniform slurry. Another 700 mL of 30% HBr in acetic acid solution (2 ml/g NCA starting material) was added in one lot at 25-30° C. and mixed for 18 hours. The mixing was stopped and the precipitate was allowed to settle for 15 minutes. The supernatant was decanted, 3,500 mL of acetone was added to the solids and mixed for 5 minutes, followed by decanting the supernatant. This acetone addition, mixing, and decanting step was repeated twice with 2×1,750 mL of acetone. Acetone (2,000 mL) was added and the polymer was filtered on an 18.5 cm Buchner funnel, washed with 2×1,000 mL acetone, and allowed to dry under nitrogen atmosphere for 5 minutes. The polymer was dissolved in 3,500 mL deionized water and nitrogen was bubbled through the solution to remove traces of benzyl bromide.

Dialysis/ultrafiltration and lyophilization (freeze drying). The poly-L-lysine.HBr solution was dialyzed or UF against running deionized water using dialysis tubing having a molecular weight cut off of approximately 12K or a 5K membrane for UF to remove oligomers and salts. The dialyzed or UF solution was collected, filtered through a 0.2 micron filter, and lyophilized (freeze dried) to get the solid poly-L-lysine-.HBr polymer. The yield was 75.5%. $^1$H NMR showed the complete removal of the Cbz group (absence of aromatic peak). The viscosity was measured in a 1 wt. % aqueous solution at 25° C. and the viscosity molecular weight was calculated as 27,700 Daltons.

Hydrolysis. The time required to hydrolyze the polymer using 48% aqueous HBr to the desired molecular weight (5,500-12,000 Daltons by GPC MALLS) was calculated as 152.4 hours (6.35 days) using the formula described in Example 1. The polymer (179.0 g) was dissolved in 2,828 mL deionized water to form a clear solution, mixed for 15 minutes, and 1,454 mL of 48% aqueous HBr was added and mixed for 152.4 hours.

The hydrolyzed poly-L-lysine.HBr solution was dialyzed or UF against running deionized water using dialysis tubing having a molecular weight cut off of approximately 12K or a 1K membrane for UF to remove oligomers and salts. The dialyzed or UF solution was collected, filtered through a 0.2 micron filter and lyophilized (freeze dried) to get the solid poly-L-lysine.HBr polymer. The yield was 53%. The molecular weight measured by GPC MALLS was 7,600 Daltons and the viscosity was measured in a 1 wt. % aqueous solution at 25° C. to calculate the viscosity molecular weight of 14,200 Daltons.

Example 3

Preparation of Poly-L-Lysine.HBr Polymer

Polymerization. $N^{68}$-Cbz-L-Lysine NCA (7,500 g, 24.51 mole) was transferred to a 100 gallon reactor equipped with a cooling/heating jacket and dissolved in 49 liter of 1,4-dioxane to make an approximately 0.5 M solution at a temperature of 25 to 30° C. A solution of 2,451 mL of 1 N sodium methoxide in methanol was prepared and added to the NCA solution in one portion with vigorous mixing. The polymerization solution was mixed for 2 hours and then maintained at 25 to 30° C. for 18 to 24 hours.

Deprotection of Cbz group. The protected polymer, poly-Cbz-L-Lysine in 1,4-dioxane solution was diluted with 73.5 liter of 1,4-dioxane to make a solution having a 0.2M concentration based on the amount of NCA starting material. A solution of 30% HBr in acetic acid (15,000 mL, 2 mL/g NCA starting material) was added to the polymer solution slowly with vigorous mixing over 60 minutes at a temperature of 25 to 30° C. The polymer began precipitating after the addition of about 7,500 mL of HBr in acetic acid solution. The resultant mixture was mixed at a temperature of 25 to 30° C. for 45 minutes to form a uniform slurry. Another portion of HBr in acetic acid (15,000 mL, 2 mL/g NCA) was added in one lot at a temperature of 25 to 30° C. and mixed for 18 hours. The mixing was stopped and the precipitate was allowed to settle for 30 minutes. The supernatant was decanted and 75 liter of acetone was added to the solids and mixed for 10 minutes, followed by decanting of the supernatant. This step was repeated twice with 2×37.5 liter of acetone. Acetone (40 liter) was added and the polymer was filtered on a glass-lined contained filter. The polymer was washed with 2×20 liter acetone and dried under nitrogen atmosphere for 15 minutes. The polymer was dissolved in 75 liter of deionized water and nitrogen was bubbled through the solution to remove traces of benzyl bromide.

Dialysis/ultrafiltration and lyophilization (freeze drying). The poly-L-lysine.HBr solution was dialyzed or UF against running deionized water using dialysis tubing having a molecular weight cut off of approximately 12K or a 5K membrane for UF to remove oligomers and salts. The dialyzed or UF solution was collected, filtered through a 0.2 micron filter, and lyophilized (freeze dried) to get the solid poly-L-lysine-.HBr polymer. The yield was 68.3%. $^1$H NMR showed the complete removal of the Cbz group (absence of aromatic peak). The viscosity was measured in a 1 wt. % aqueous solution at 25° C. and the viscosity molecular weight was calculated as 41,200.

Hydrolysis. The time required to hydrolyze the polymer using 48% aqueous HBr to the desired molecular weight (5,500-12,000 Daltons by GPC MALLS) was calculated as 13.1 days (314.4 hours) using the formula described in Example 1. The polymer (3,500 g) was dissolved in 55.3 liter deionized water to form a clear solution and mixed for 30 minutes. An aqueous solution of 48% HBr (28.4 liter) was added and mixed for 314 hours.

The hydrolyzed poly-L-lysine.HBr solution was dialyzed or UF against running deionized water using dialysis tubing having a molecular weight cut off of approximately 12K or a 1K membrane for UF to remove oligomers and salts. The dialyzed or UF solution was collected, filtered through a 0.2 micron filter and lyophilized (freeze dried) to get the solid poly-L-lysine.HBr polymer. The yield was 50.2%. The molecular weight was measured by GPC MALLS as 9,300 Daltons and the viscosity was measured in a 1 wt. % aqueous solution at 25° C. and the viscosity molecular weight was calculated as 17,300 Daltons.

Example 4

Preparation of Poly-L-Lysine.HBr Polymer

Polymerization. N$^{68}$-Cbz-L-Lysine NCA (25,490 g, 83.3 moles) was transferred to a 200 gallon reactor equipped with cooling/heating jacket to maintain the temperature at 25 to 30° C. and dissolved in 155 liter of 1,4-dioxane to make a solution having a NCA concentration of about 0.5 M. A solution was prepared by combining 8,227 mL of 1N sodium methoxide (8.227 moles) with methanol and this solution was added to the NCA solution in one portion with vigorous mixing. The polymerization solution was mixed for 2 hours and the temperature was maintained at 25 to 30° C. for 18 to 24 hours.

Deprotection of Cbz group. The protected polymer, poly-Cbz-L-Lysine in a 1,4-dioxane solution was diluted with 204 liter of 1,4-dioxane to make a solution having a concentration of about 0.2M based on the amount of NCA starting material. A solution of 30% HBr in acetic acid (50.4 liter, 2 ml/g NCA starting material) was added into the polymer solution slowly with vigorous mixing in 60 minutes at a temperature of 25 to 30° C. The polymer started precipitating after about 25 liters of the HBr in acetic acid solution was added. The resultant mixture was mixed at a temperature of 25 to 30° C. for 30 minutes to form a uniform slurry. A solution of HBr in acetic acid (50.4 liter, 2 ml/g NCA starting material) was added in one lot at a temperature of 25 to 30° C. and mixed for 18 hours. The mixing was stopped and the precipitate was allowed to settle for 30 minutes. Ice-cold acetone (383 liter) was added to the solids, mixed for about 30 minutes, and filtered through a glass-lined filter. The solids were washed with 3×172 liter of acetone and allowed to dry under a nitrogen atmosphere for 15 minutes. The polymer was dissolved in about 235 liter deionized water and nitrogen was bubbled through the solution to remove traces of benzyl bromide.

Dialysis/ultrafiltration and lyophilization (freeze drying). The poly-L-lysine.HBr solution was dialyzed or UF against running deionized water using dialysis tubing having a molecular weight cut off of approximately 12K or a 5K membrane for UF to remove oligomers and salts. The dialyzed or UF solution was collected, filtered through a 0.2 micron filter, and 150 mL was lyophilized (due to a very large volume of the solution to be lyophilized) to get the solid weight for poly-L-lysine.HBr polymer. The total solids weight was calculated based on the estimated total volume. The yield was estimated to be about 55%. $^1$H NMR showed the complete removal of the Cbz group (absence of aromatic peak). The viscosity of the polymer in a 1 wt. % aqueous solution was measured at 25° C. and the viscosity molecular weight was calculated as 32,360 Daltons.

Hydrolysis. The time required to hydrolyze the polymer using 48% aqueous HBr to the desired molecular weight (5,500-12,000 Daltons by GPC MALLS) was calculated as 208.3 hours (9.17 days) using the formula described in Example 1. An aqueous 48% HBr was added to the polymer solution in an amount to produce a 0.3 M HBr concentration. This solution was mixed for 220 hours.

The hydrolyzed poly-L-lysine.HBr solution was dialyzed or UF against running deionized water using a dialysis tubing having a molecular weight cut off of approximately 12K or a 1K membrane for UF to remove oligomers and salts. The dialyzed or UF solution was collected, filtered through a 0.2 micron filter, and lyophilized (freeze dried) to get the solid poly-L-lysine.HBr polymer. The yield was 52%. The molecular weight measured by GPC MALLS was 8,100 Daltons and the viscosity was measured in a 1 wt. % aqueous solution at 25° C. and the viscosity molecular weight was calculated as 14,800 Daltons.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above processes without departing from the scope of the invention, it is intended that all matter contained in the above description shall be interpreted as illustrative and not in a limiting sense.

What is claimed is:

1. A process for the preparation of a polylysine polymer comprising repeating units corresponding to Formula 3 or a salt thereof and having a lysine-basis weight average molecular weight from about 5,500 to about 12,000 Daltons, the process comprising:
   hydrolyzing a polylysine intermediate comprising repeating units corresponding to Formula 3 or a salt thereof and having a lysine-basis weight average molecular weight from about 12,500 to about 22,000 Daltons, wherein Formula 3 has the structure:

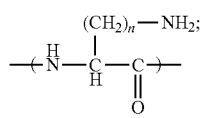

Formula 3 n is 4; and
wherein said polylysine polymer is a homopolymer of lysine.

2. The process as set forth in claim 1 wherein preparation of said polylysine intermediate comprises
removing a nitrogen protecting group from a protected polylysine intermediate comprising repeating units of Formula 2 or a salt thereof and having a lysine-basis weight average molecular weight from about 12,500 Daltons to about 22,000 Daltons, wherein
Formula 2 has the structure:

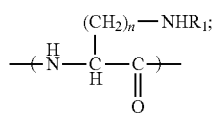

Formula 2

$R_1$ is an amino protecting group; and
n is 4.

3. The process as set forth in claim 2 wherein preparation of said protected polylysine intermediate comprises polymerizing an N-carboxyanhydride compound of Formula 1, wherein
Formula 1 has the structure:

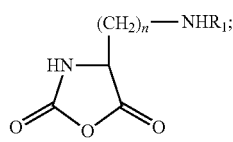

Formula 1

$R_1$ is an amino protecting group; and
n is 4.

4. The process of claim 2 wherein hydrolyzing the polylysine intermediate and removing the nitrogen protecting group from the protected polylysine intermediate are carried out concurrently.

5. The process of claim 2 wherein the amino protecting group is carbobenzyloxy, t-butoxycarbonyl, or allyloxycarbonyl.

6. The process of claim 3 wherein the polymerization is conducted in the presence of an initiator.

7. The process of claim 6 wherein the initiator comprises a metal alkoxide.

8. The process of claim 3 wherein the polymerization is conducted in an organic solvent medium and deprotection of the N-protected polylysine intermediate comprises introducing a combination of a mineral acid and an organic acid into said polymerization medium, thereby forming a precipitate comprising repeating units consisting of the $N^\epsilon$-salt of the repeating units of Formula 3 and said mineral acid.

9. The process of claim 3 comprising removing oligomers and other low molecular weight components from a solution comprising the deprotected polylysine intermediate prior to hydrolysis of said deprotected intermediate.

10. The process of claim 9 wherein the deprotected polylysine intermediate and associated oligomers and/or other low molecular weight components are taken up into an aqueous medium, and the aqueous medium containing the deprotected intermediate polymer and oligomers and/or other low molecular weight components is contacted with a surface of a dialysis membrane having an aqueous medium on the opposite surface thereof into which oligomers and other low molecular weight components are received in the dialysis, thereby producing a retentate comprising deprotected polylysine intermediate of reduced oligomer content.

11. The process of claim 10 wherein the retentate is lyophilized to yield solid deprotected polylysine.

12. The process of claim 11 wherein the solid deprotected polylysine is taken up into an aqueous solution wherein it is contacted with a mineral acid for the hydrolysis.

13. The process of claim 2 wherein the hydrolysis of the deprotected polylysine intermediate is carried out for a reaction time calculated from the viscosity molecular weight of the deprotected polylysine intermediate.

14. The process of claim 3 wherein the polymerization of the N-carboxyanhydride compound is conducted in a polymerization reaction medium comprising a nonpolar solvent.

15. The process of claim 3 wherein the yield of polylysine polymer is greater than about 45% based on the quantity of the N-carboxyanhydride starting material.

16. The process of claim 1 wherein the polylysine polymer is poly-L-lysine, poly-D-lysine, or a racemic mixture thereof.

17. The process of claim 13 wherein an algorithm is used to calculate the hydrolysis reaction time, the algorithm being:

Time Required =[(viscosity molecular weight of unhydrolyzed polymer−21,000) ×0.012]+ 72(±10%) hours.

18. The process of claim 1 wherein the polylysine polymer comprising repeating units corresponding to Formula 3 or a salt thereof and having a lysine-basis weight average molecular weight from about 5,500 to about 12,000 Daltons has a polydispersity index of about 1.2 to about 1.5.

19. A process for the preparation of a polylysine or polyornithine polymer comprising repeating units corresponding to Formula 3 or a salt thereof and having a lysine-basis or ornithine-basis weight average molecular weight from about 5,500 to about 12,000 Daltons, the process comprising:
hydrolyzing a polylysine or polyornithine intermediate comprising repeating units corresponding to Formula 3 or a salt thereof and having a lysine-basis or ornithine-basis weight average molecular weight from about 12,500 to about 22,000 Daltons, wherein
Formula 3 has the structure:

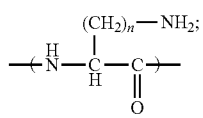

Formula 3 n is 3 or 4; and
the hydrolysis of the polylysine or polyornithine intermediate is carried out for a reaction time calculated according to an algorithm, the algorithm being:

Time Required =[(viscosity molecular weight of unhydrolyzed polymer−21,000) ×0.012]+ 72(±10%) hours.

* * * * *